US012582542B2

(12) United States Patent
Bauerfeind

(10) Patent No.: US 12,582,542 B2
(45) Date of Patent: Mar. 24, 2026

(54) STABILIZING ROD FOR AN ORTHOPEDIC AID

(71) Applicant: Bauerfeind AG, Zeulenroda-Triebes (DE)

(72) Inventor: Hans B. Bauerfeind, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 0 days.

(21) Appl. No.: 17/042,036

(22) PCT Filed: Mar. 22, 2019

(86) PCT No.: PCT/EP2019/057289

§ 371 (c)(1),
(2) Date: Sep. 25, 2020

(87) PCT Pub. No.: WO2019/185485

PCT Pub. Date: Oct. 3, 2019

(65) Prior Publication Data

US 2021/0030576 A1 Feb. 4, 2021

(30) Foreign Application Priority Data

Mar. 27, 2018 (DE) ..................... 10 2018 204 640.9

(51) Int. Cl.
*A61F 5/01* (2006.01)
(52) U.S. Cl.
CPC ................................. *A61F 5/0109* (2013.01)
(58) Field of Classification Search
CPC ........ A61F 5/0109; A61F 5/01; A61F 5/3707; A61F 5/0118; A61F 5/0106; A61F 5/0123; A61F 5/012; A61F 2005/0179; A61F 2005/0137

USPC .......................................................... 602/26
See application file for complete search history.

(56) References Cited

U.S. PATENT DOCUMENTS

| | | | | |
|---|---|---|---|---|
| 1,142,045 | A | * | 6/1915 | Mcleod .................... A41C 1/14 2/259 |
| 3,351,954 | A | * | 11/1967 | Chalfin .................... A41C 1/14 450/41 |
| 5,607,415 | A | * | 3/1997 | Datta ................ A61F 13/15699 604/386 |
| 2005/0038367 | A1 | * | 2/2005 | McCormick .......... A61F 5/0106 602/26 |

(Continued)

FOREIGN PATENT DOCUMENTS

FR 2997294 A1 * 5/2014 ........... A61F 5/0123

OTHER PUBLICATIONS

International Preliminary Report on Patentability for PCT/EP2019/057289 dated Oct. 1, 2020, 8 pages.

*Primary Examiner* — Alireza Nia
*Assistant Examiner* — Michael Milo
(74) *Attorney, Agent, or Firm* — Sheppard Mullin Richter & Hampton LLP

(57) ABSTRACT

The invention relates to a stabilizing rod (10) for an orthopedic aid, the stabilizing rod (101) having in the longitudinal direction a first section (110) and a second section (120), the first section (110) and the second section (120) being connected to each other via a third, flexible section (130). According to the invention, the third, flexible section (130) has at least one material cut-out (131).

20 Claims, 6 Drawing Sheets

(56) References Cited

U.S. PATENT DOCUMENTS

2007/0167891 A1* 7/2007 Gramza ............... A61F 5/0106
                                                          602/5
2017/0203076 A1* 7/2017 Groneberg ........ A61M 25/0054
2019/0048923 A1* 2/2019 Gunnsteinsson ......... E05D 1/00

* cited by examiner

STABILIZING ROD FOR AN ORTHOPEDIC AID

This application is a U.S. National Stage Application under 35 U.S.C. 371 of International Application No. PCT/EP2019/057289, filed Mar. 22, 2019, which claims priority to German Patent Application 10 2018 204 640.9, filed Mar. 27, 2018.

The present invention relates to stabilizing rods for an orthopedic aid, in particular knee bandages and orthopedic aids, comprising at least one stabilizing rod according to the invention.

The use of stabilizing rods in orthopedic aids is known. WO 2011/035885 A1 and DE 3637 879 A1 disclose knee joint bandages, short knee bandages, with lateral stabilizing rods. Stabilizing rods made of metal, which are flexible as a result of their construction as spring band rods, i.e. flat-pressed coils of a helical spring, are used. However, since such stabilizing rods are often welded to the textile of the orthopedic aid, at least partial regions of the metallic spring band rods must be laminated with a weldable plastic. In addition, the metal can destroy the adjacent textile. The flat spiral springs used are equally elastic over the entire course of the spring and the degree of inflection cannot be limited.

The technical problem on which the present invention is based is the provision of improved stabilizing rods for an orthopedic aid, in particular knee bandages, which work at least as well as the stabilizing rods from the prior art, but are simpler and less expensive to produce, can be easily welded, are lighter and/or protect the adjacent textile.

The present invention solves this technical problem by means of a stabilizing rod according to claim 1.

In particular, the present invention solves the technical problem on which it is based by means of a stabilizing rod for an orthopedic aid, wherein the stabilizing rod has a flexible section, the flexible section having at least one material cut-out.

The flexible section preferably has multiple material cut-outs. The flexible section can extend over the entire length of the stabilizing rod or only make up a part of the length of the stabilizing rod.

The present invention preferably solves the technical problem on which it is based by means of a stabilizing rod for an orthopedic aid, in particular for a knee bandage, wherein the stabilizing rod has in the longitudinal direction a first section and a second section, the first section and the second section being connected to each other via a third, flexible section, characterized in that at least the third, flexible section has at least one material cut-out.

In particular, the present invention solves the technical problem on which it is based by means of a stabilizing rod for an orthopedic aid, in particular for a knee bandage, wherein the stabilizing rod has in the longitudinal direction a first section and a second section, the first section and the second section being connected to each other via a third, flexible section, characterized in that the third, flexible section has at least one material cut-out.

The third flexible section preferably as multiple material cut-outs.

The flexible section preferably has a plurality of material cut-outs. The plurality of cut-outs is preferably arranged on one side of the stabilizing rod. The side of the stabilizing rod which forms the inner, concave side when the stabilizing rod is bent is preferably provided with the plurality of cut-outs.

The first section and the second section preferably do not have multiple material cut-outs. The first section and/or the second section can, however, alternatively also have material cut-outs, for example if these sections are also to be designed to be flexible.

The length and positioning of the flexible section can advantageously determine the position and strength of the flexibility of the stabilizing rod.

The third flexible section preferably has three to fifteen material cut-outs. The third flexible section preferably has four to ten material cut-outs. The third flexible section preferably has four to fifteen material cut-outs. The third flexible section preferably has at least four material cut-outs. The third flexible section preferably has seven to twelve material cut-outs.

In particular, the material cut-outs can be designed as incisions. The third section is therefore preferably designed in the form of a toothed rack as a result of the multiple incisions.

Surprisingly, it was found that the material cut-outs according to the invention with the teeth lying in between can limit the flexion angle of the stabilizing rod when the teeth abut each other as a result of the bending of the rod. If the stabilizing rod is bent so that all the teeth lying between the incisions abut each other, further flexion is only possible by twisting the stabilizing rod, which the person wearing the orthopedic aid can feel directly and thus receives feedback on the flexion limitation.

Surprisingly, it was also found that good and sufficient flexibility of the stabilizing rod can be achieved through such material cut-outs without the stabilizing bar having to be designed as a spring band rod. Furthermore, only a central region of the stabilizing rod having material cut-outs proved sufficient for the flexibility. Since no spring band rod, in particular a continuous spring band rod, is necessary, metal and/or the circularly overlapping spring band can advantageously be dispensed with, whereby the stabilizing rod protects the adjacent textile. The stabilizing rod can also advantageously be manufactured in one piece and from plastics, as a result of which a costly lamination step is omitted and the stabilizing rod can be designed more easily.

The flexible region of the stabilizing rod can be determined by the position of the flexible section along the length of the stabilizing rod.

If the flexible section extends over the entire length of the stabilizing rod, the flexible or particularly flexible region of the stabilizing rod can be determined by the material thickness of the respective sections, in that the particularly flexible section has a lesser material thickness.

In a preferred embodiment, the stabilizing rod is in one piece. In a preferred embodiment, the stabilizing rod consists of a single material. In a preferred embodiment, the stabilizing rod consists of a plastic.

Alternatively, however, it can also be provided, for example, that a chord made of metal is incorporated into the plastic of the stabilizing rod. Even if the chord is made of metal, it is still lighter than a spring band rod. If a chord made of a harder material than the material of the stabilizing rod, in particular a chord made of metal, is embedded in the stabilizing rod, the stabilizing rod can be designed to be thinner and still retain its restoring force.

Preferably, the deeper the material cut-outs are, the further away they are from the central region of the flexible section.

Preferably, the deeper the material cut-outs in the third section are, the further away they are from the central region of the third flexible section.

The material cut-outs are preferably only on one side of the third section.

The third section is preferably tapered compared to the first and second sections.

The third section is preferably tapered compared to the first and second sections in relation to the width of the section, in particular the width of the base body.

The material cut-outs, in particular incisions, are preferably not circular, but are narrower towards the edge of the stabilizing rod and particularly preferably form the shape of a keyhole. This is particularly preferably achieved in that the material cut-outs are formed by tooth-like material elevations lying between the material cut-outs, wherein these tooth-like material elevations are preferably shaped like a hammer or zipper tooth, i.e. longer towards the edge of the stabilizing rod than towards the center of the base body. Such a material cut-out, in particular an incision, that is not circular but is shaped like a keyhole, has the advantage that stress peaks in the material are reduced when the stabilizing rod is bent.

The first section and the second section are preferably less flexible than the third section. If the stabilizing rod according to the invention is preferably used in a knee bandage, it is in particular attached to the knee bandage in such a way that the third section is positioned at the level of the knee bandage. It is precisely in this region that the stabilizing rod must be flexible, so that it is sufficient if the first section and the second section are less flexible.

The width of the third, flexible section is preferably less than the width of the first section and the width of the second section of the stabilizing rod.

The stabilizing rod preferably has a length, a width and a height, the width of the first section and the width of the second section being greater than the height of the stabilizing rod. The stabilizing rod preferably has a length, a width and a height, the width of the first section and the width of the second section being greater than the height of the stabilizing rod and the width of the third, flexible section being less than the width of the first section and the width of the second section.

The stabilizing rod preferably has at least one longitudinal groove, in particular one or two longitudinal grooves. The third central region of the stabilizing rod, in particular in the base body, preferably has at least one longitudinal groove, in particular one or two longitudinal grooves. Advantageously, such grooves make it possible not only to bend the stabilizing rod along the toothing, but also to bend it in a direction offset by 90°, which is particularly advantageous when applying and removing a bandage which has such a stabilizing rod.

In a preferred embodiment, the third, central section has the same or greater material thickness in relation to the height of the stabilizing rod, relative to the material thickness of the first and second sections. Alternatively, it can also be provided that the height of the third central region is varied, for example that it is varied in a wave-like manner. It can preferably be provided that the central region is thickened or thinned, in particular thickened, at the points where material cut-outs are provided, and thinned or thickened, in particular thinned, at the points where tooth-like material elevations adjoin, resulting in a wave shape.

In a preferred embodiment, the base body of the stabilizing rod is thickened in height in the transition region from the first section to the third section and/or from the second section to the third section. Advantageously, this better defines the bending point already defined by the toothing. The thickened portion can preferably be shaped as a bead.

In a preferred embodiment, the base body of the rod is at least partially wedge-shaped. Particularly preferably, the base body is wedge-shaped in the third central region, in particular is designed in such a way that it tapers in the direction of the tooth-like elevations. This design advantageously promotes easier bending of the rod, since the compression of the material is greatest in the region of the bending point.

In a preferred embodiment, the base body has a greater material thickness in the third, central region, i.e. is higher than the first and/or the second region.

In a preferred embodiment, at least partial regions of the surface of the stabilizing rod are not smooth but roughened. This has the advantage of preventing the rod, for example when it is in a plastic-coated terrycloth pocket of a bandage, from squeaking when the knee is bent. In particular, the flat sides of the stabilizing rod are preferably roughened.

The first and/or the second section of the stabilizing rod, in particular the first section of the stabilizing rod, preferably has a gripping piece. The gripping piece is preferably designed as an eyelet. The eyelet preferably has a thickened portion on its side facing away from the stabilizing rod. As an alternative to an eyelet, the at least one gripping piece can also have knobs on the stabilizing rod, which make it easier to grip the rod when it is applied and removed.

In a preferred embodiment, the first and the second section of the stabilizing rod each have a gripping piece. Both gripping pieces are preferably designed as an eyelet. In this embodiment, the first gripping piece can advantageously be used as a pull-on aid and the second gripping piece as a pull-off aid.

The stabilizing rod is used here with a double effect, namely on the one hand to stabilize the knee joint and on the other hand as a pull-on and pull-off aid, for which the stabilizing rod is provided with at leak one gripping piece which is easy to grip and transfers a pull exerted on it directly to the bandage material. It can be formed at the upper and/or lower end of the stabilizing rod. When the gripping piece is pulled, it is introduced into the bandage over the entire length of said bandage. The gripping piece is expediently designed as an eyelet in which the passage through its hole is approximately at right angles to the bandage material. With such a design of the gripping piece, it can be gripped directly with a finger, which passes through the eyelet and in this way conveniently transfers the tension to the bandage. The gripping of the eyelet can furthermore be facilitated in that it has a thickened portion on its side facing away from the stabilizing rod. This makes it easier to grip the bandage with the fingers when applying or removing said bandage.

Surprisingly, it was found that the stabilizing rod, despite a tapered third section with several material cut-outs, is still stable enough to be used as a pull-on aid.

The stabilizing rod according to the invention is preferably a stabilizing rod for a bandage The stabilizing rod according to the invention is preferably a stabilizing rod for a knee joint bandage.

The present invention also relates to the use of a stabilizing rod according to the invention in an orthopedic aid, in particular a bandage, preferably a knee joint bandage comprising a stabilizing rod according to any of the preceding claims.

The present invention also relates to an orthopedic aid comprising a stabilizing rod according to the invention. The orthopedic aid is preferably a bandage. The orthopedic aid is particularly preferably a knee bandage or a knee joint bandage. The base body of the knee bandage or knee joint bandage is preferably formed from a textile, in particular a knitted fabric. Suitable knee bandages or knee joint bandages and their base bodies are known to a person skilled in the art.

The present invention therefore also relates to a knee joint bandage comprising a stabilizing rod according to the invention.

A knee joint bandage is preferred, wherein the third flexible section of the stabilizing rod is at the level of the knee when the knee joint bandage is in the applied state.

The knee joint bandage preferably has two stabilizing rods, in particular two stabilizing rods according to the invention.

A knee joint bandage is preferred, wherein the knee-joint bandage has two stabilizing rods, in particular two stabilizing rods according to the invention, the stabilizing rods extending over the length of the knee joint bandage. The stabilizing rods preferably extend to the side of the knee over the length of the knee joint bandage.

A knee joint bandage is preferred, wherein the third flexible section of the stabilizing rods is at the level of the knee when the knee joint bandage is in the applied state.

The material cut-outs are preferably only on one side of the third section. The material cut-outs are preferably on the side of the third section pointing away from the knee. This advantageously leads to the fact that when the knee is bent, the third section is bent in such a way that the tooth-like elements lying between the material cut-outs abut after a certain bending distance and thus limit the movement.

The at least one stabilizing rod is preferably embedded in a pocket arranged on the bandage. A partial region of the at least one stabilizing rod is preferably welded to the textile of the bandage and/or the pocket.

Preference is given to a bandage made of elastic material, in particular a textile, in particular a knee joint bandage, which is provided on at least one side with a stabilizing rod according to the invention extending over the length of the bandage, wherein the stabilizing rod is provided with one or two gripping pieces and is embedded in a pocket arranged on the bandage, which is firmly connected to the material of the bandage via edge zones and at its end arranged above the kneecap. The stabilizing rod is preferably welded essentially continuously to the material of the bandage. The gripping piece is preferably designed as an eyelet in which the passage through its hole is approximately at right angles to the bandage material. The side facing away from the stabilizing rod preferably has a thickened portion.

The knee joint bandage preferably has a pad associated with the kneecap.

Further preferred embodiments result from the subclaims, the examples and the drawings.

FIG. 1 shows a stabilizing rod according to the invention;

Figure 1:
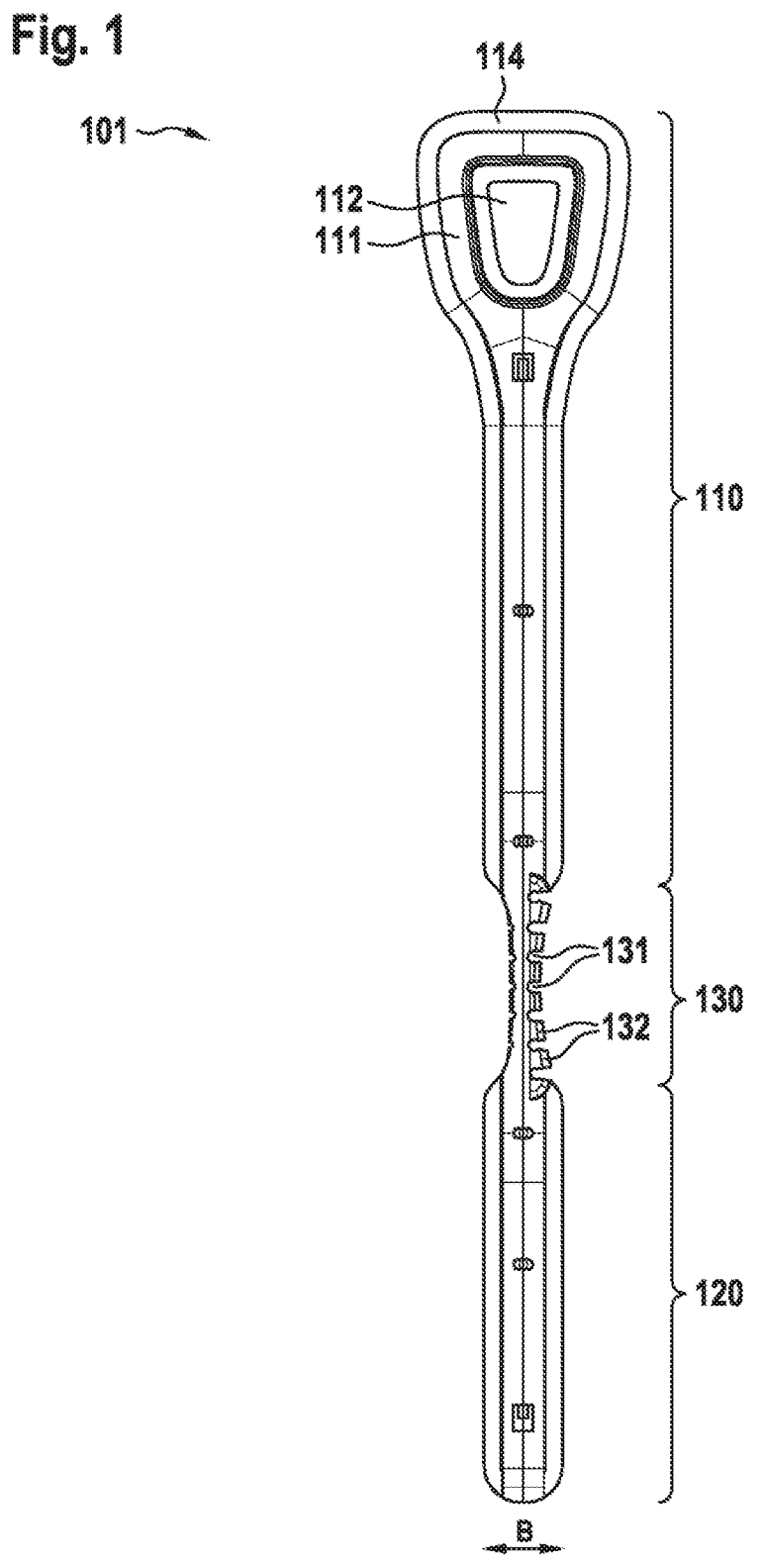
Figure 6:
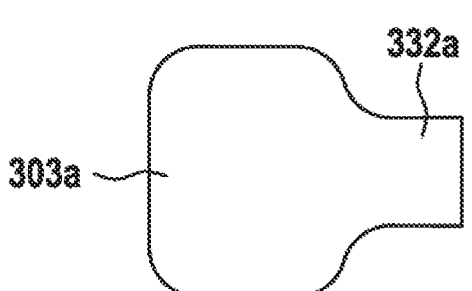
Figure 6:
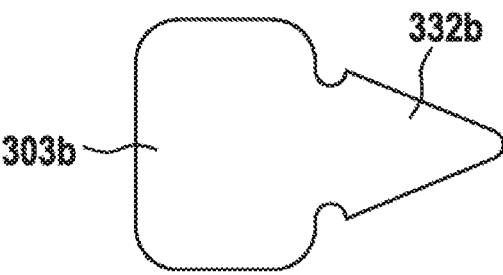
Figure 6:
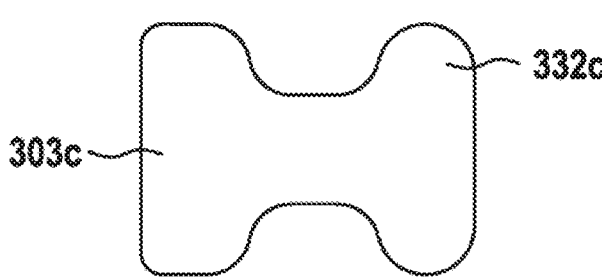
Figure 6:
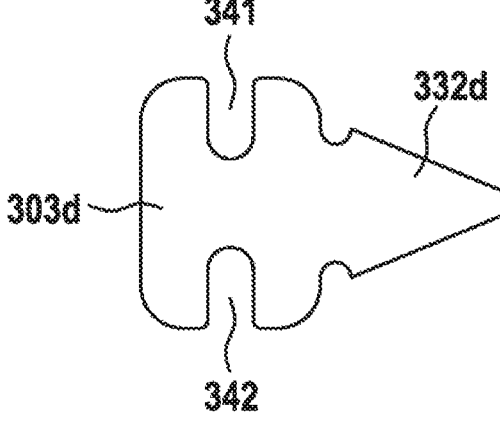

FIG. 6 shows different embodiments of the cross section of the central region of a stabilizing rod according to the invention. FIG. 1 shows a stabilizing rod 101 according to the invention. The stabilizing rod 101 is formed in one piece and molded from a plastic. According to the invention, the stabilizing rod 101 is divided into a first section 110, a second section 120 and a third section 130, which connects the first section 110 and the second section 120 to each other. The third section 130 is tapered in its width B compared to the first and second sections 110, 120 and furthermore has seven material cut-outs 131. The deeper the material cut-outs 131 are, the further away they are from the central region of the third flexible section 130. As a result, the third section 130 of the stabilizing rod 101 is more flexible than the first section 110 and the second section 120. In particular, a bending of the third section 130 in the direction of the cut-outs 131 is provided so that the tooth-like material elevations 132 lying between the cut-outs 131 abut each other and thereby cushion and limit the bending.

Such a stabilizing rod can advantageously enable the flexing movement in the pivoting region of the knee axis by being divided into the three sections, but remain stable and stiffening in the other regions. A defined bending point is made possible while at the same time defining the maximum flexion angle.

The first section 110 of the stabilizing rod 101 has a gripping piece 111 which forms a hole 112. The gripping piece 111 is part of the first section 110 and is formed in one piece from its material. The upper region of the gripping piece 111 has a thickened portion 114 through which the gripping piece 111 can be gripped and pulled more easily.

Figure 2:
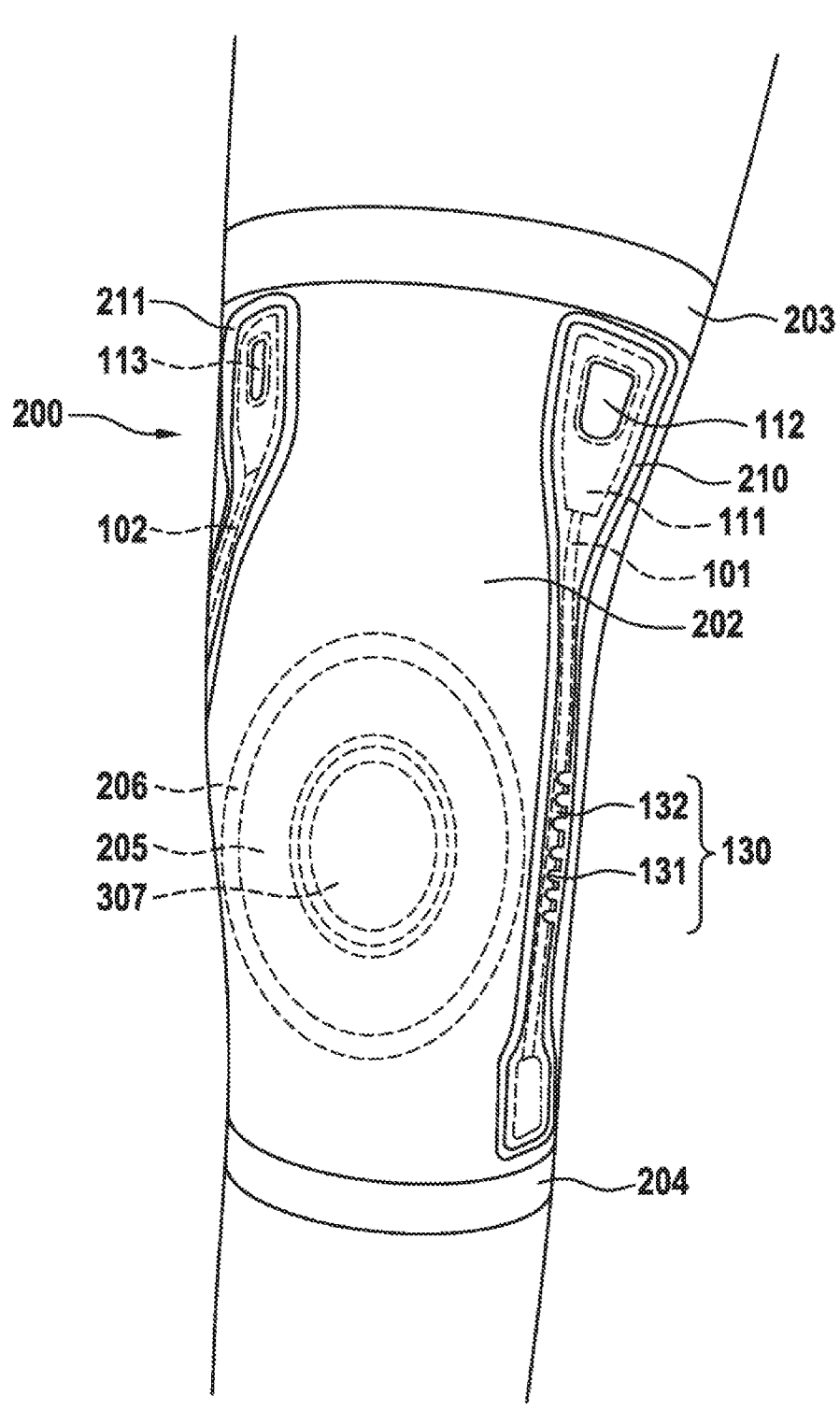
FIG. 2 shows a knee joint bandage according to the invention with two stabilizing rods from FIG. 1.

The knee joint bandage 200 shown in FIG. 2 consists of a stocking 202 made of elastic textile material and it is provided with the two edges 203 and 204 at both ends, which help to prevent the bandage 200 from slipping. In addition, these edges 203 and 204 are made of a material that has a lower tension than the stocking 202 in order to constrict the wearer's leg only slightly at the relevant points. On the front side of the knee joint, a profile insert with the pad 205 is incorporated into the stocking 202, which may consist of foam or silicone, for example, and which has considerable elasticity. The pad 205 is covered on the inside of the stocking 202 by a cover which is connected at its edges 206 to the stocking 202, for example by gluing. In its central part, the pad 205 leaves a free region into which the kneecap 307 fits. The kneecap 307 is thus surrounded by the pad 205. To this extent, it is a knee joint bandage designed in a known manner. In addition to the pad 205, the bandage 200 is provided with two stabilizing rods 101 and 102 according to the invention, which extend essentially over the entire length of the bandage 200 and which ensure that the bandage 200 applied to the leg cannot contract in terms of its longitudinal direction. Each of the two stabilizing rods 101 and 102 is received in a pocket glued to the bandage 200 by means of the edge zone 210 or 211 to the material of the bandage 200. Depending on the desired stabilization intensity, the bandage 200 may also be provided with just one stabilizing rod. Each of the two stabilizing rods 101 and 102 has at its upper end a gripping piece 111 containing an eyelet 112 or 113, which enables the bandage 200 to be gripped with the finger when it is pulled on and pulled up along the leg and thus makes it easier to apply the bandage 200, since the bandage 200 is carried along by these and the stabilizing rod 101, 102 as a whole when the gripping pieces 111 are pulled accordingly, whereby it is easily possible to pull the bandage 200 smoothly over the foot, calf and knee into its final position. The stabilizing rods 101 and 102 contained in the pockets are fully encompassed by the relevant pockets in that their edge zones 210 and 211 are each designed as a narrow circumferential strip which is directly connected to the material of the bandage 200, for example by welding or gluing.

The particular configuration of the stabilizing rods 101, 102 preferred according to the invention is discussed in greater detail in FIG. 1. The third section 130 of the stabilizing rods 101, 102 is arranged at the level of the kneecap 307. Thus, when the knee is bent, this third section 130 is also bent. The stabilizing rods 101, 102 are positioned on the knee joint bandage 200 in such a way that the cut-outs 131 point to the rear. Thus, when the knee is bent, the tooth-like material sections 132 lying between the cut-outs 131 are pressed onto one another, as a result of which the bending process is cushioned.

Figure 3:
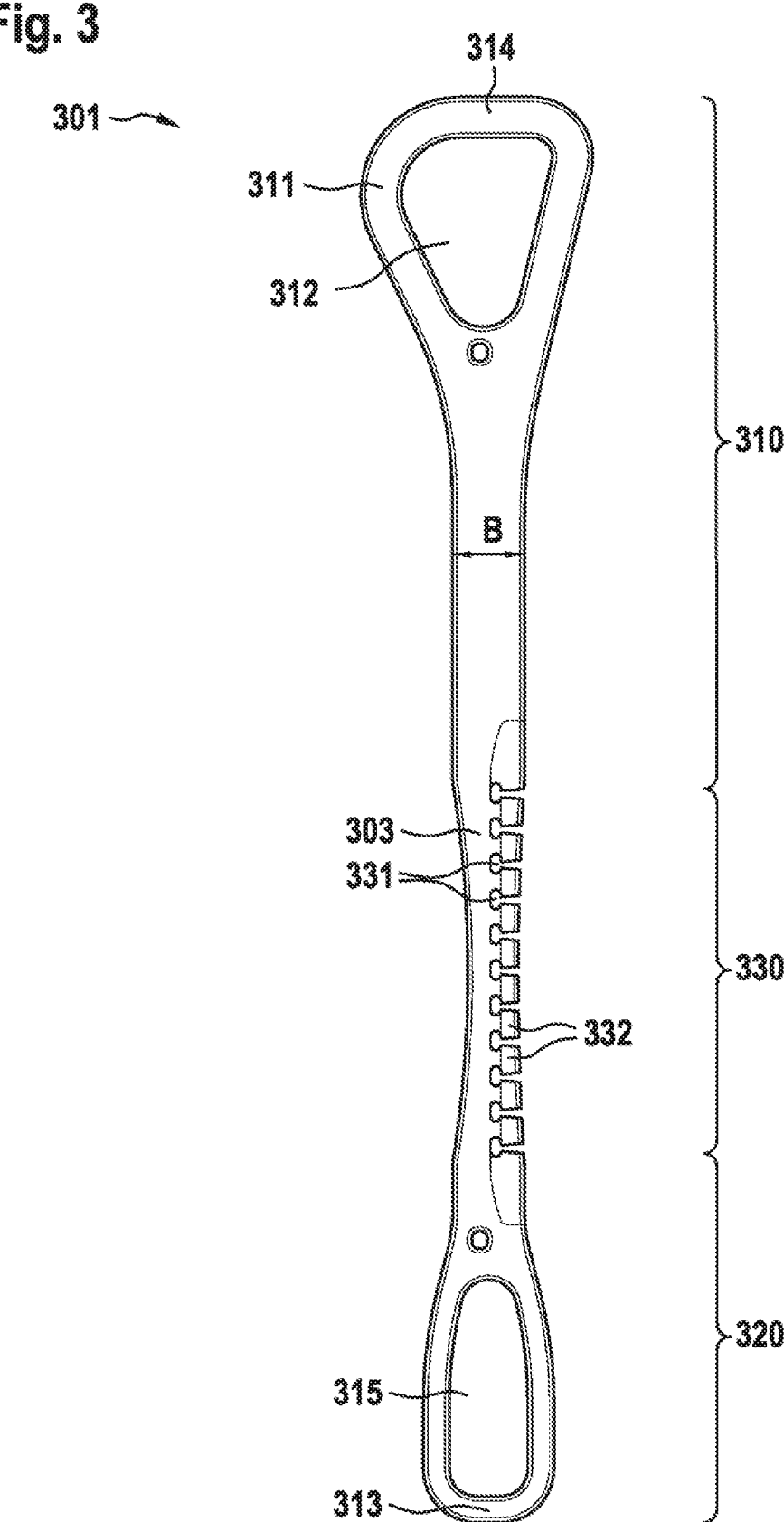
FIG. 3 shows an alternative embodiment of the stabilizing rod according to the invention.

Of course, any other stabilizing rod according to the invention can also be incorporated into a knee joint bandage as shown in FIG. 2, for example a stabilizing rod shown in FIG. 3 or a stabilizing rod with a cross section from FIGS. 6a to 6d.

Fig, 3 shows an alternative embodiment of a stabilizing rod 301 according to the invention. The stabilizing rod 301 is also formed in one piece and molded from a plastic. According to the invention, the stabilizing rod 301 is divided into a first section 310, a second section 320 and a third section 330, which connects the first section 310 and the second section 320 to each other. The sections are formed by a base body 303. The base body 303 of the third section 330 is tapered in its width B compared to the first and second sections 310, 320 and furthermore has eleven material cut-outs 331. The deeper the material cut-outs 331 are, the further away they are from the central region of the third flexible section 330. As a result, the third section 330 of the stabilizing rod 301 is more flexible than the first section 310 and the second section 320. In particular, a bending of the third section 330 in the direction of the cut-outs 331 is provided so that the tooth-like material elevations 332 lying between the cut-outs 331 abut each other and thereby cushion and limit the bending.

The tooth-like material elevations 332 have a hammer-like shape, so that the gaps in the cut-outs 331 on the lateral edge of the stabilizing rod 301 are narrower than the round ends of the cut-outs 331 in the interior of the base body 303 of the stabilizing rod 301. The cut-outs 331 shown here have a keyhole-like overall shape. In addition, the hammer head-shaped ends of the tooth-like material elevations 332 are thicker than the stem portion of the tooth-like material elevations 332. This further increases the mobility of the third section 330.

Such a stabilizing rod can also advantageously enable the flexing movement in the pivoting region of the knee axis by being divided into the three sections, but remain stable and stiffening in the other regions. A defined bending point is made possible while at the same time defining the maximum flexion angle.

The first section 310 of the stabilizing rod 301 has a gripping piece 311 which forms a hole 312. The gripping piece 311 is part of the first section 310 and is formed in one piece from its material. The upper region of the gripping piece 311 has a thickened portion 311 through which the gripping piece 311 can be gripped and pulled more easily. The second section 320 of the stabilizing rod 301 also has a gripping piece 313, which also forms a hole 315. The gripping piece 313 is part of the second section 320 and is formed in one piece from its material.

The gripping pieces 311 and 313 are suitable as a pull-on or pull-off aid for a knee joint bandage which has at least one stabilizing rod 301.

Figure 4:
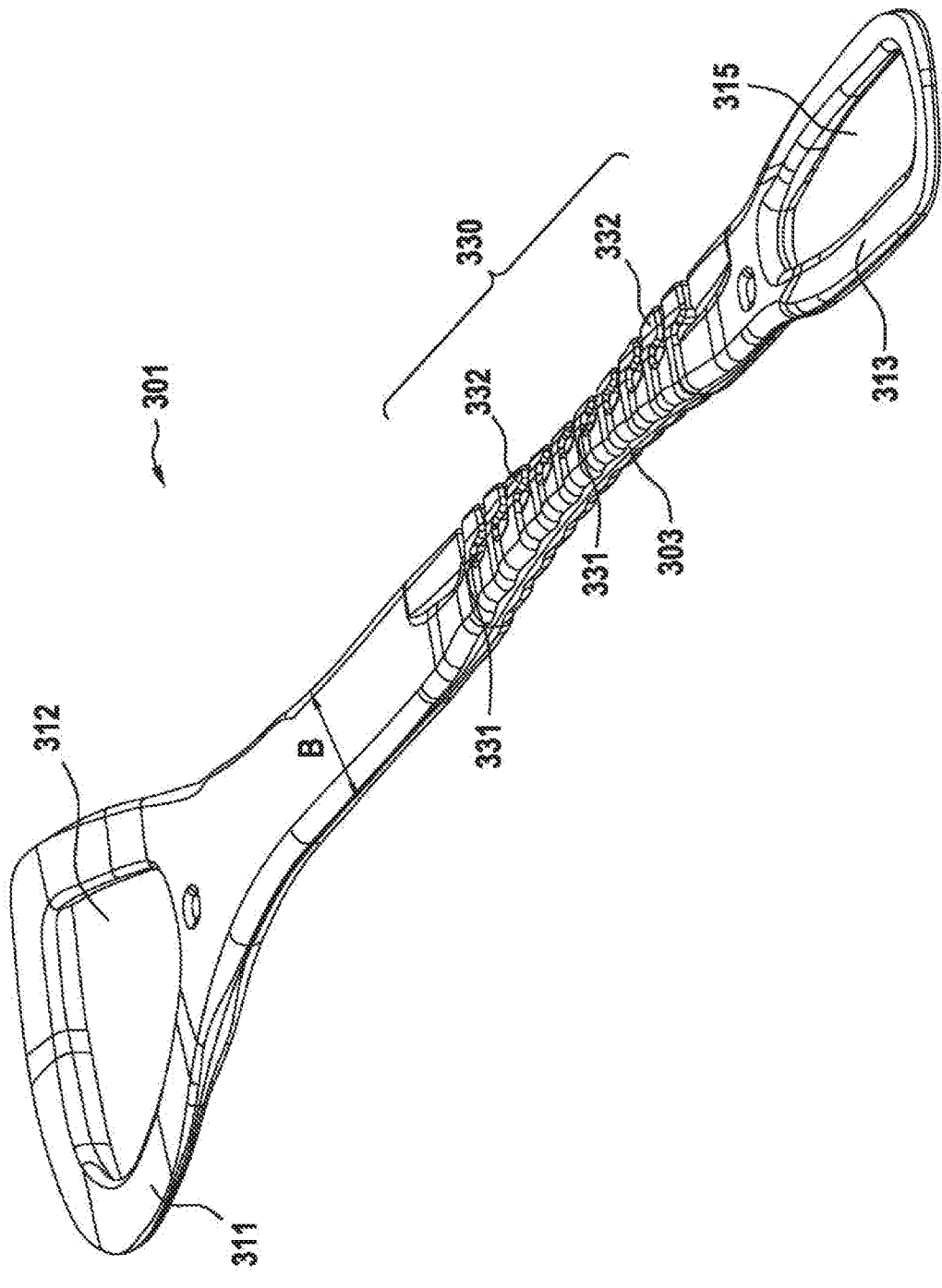
FIG. 4 shows the stabilizing rod from FIG. 3 in a different perspective.

FIG. 4 shows the embodiment of the stabilizing rod 301 from FIG. 3 in a different perspective. The flexible central section 330 with the cut-outs 331 and the tooth-like material elevations 332 as well as the gripping pieces 311 and 313 with the holes 312 and 315 can be seen again. It can be clearly seen that the width B of the base body 303 of the central section 330 is less than the width B of the other sections of the stabilizing rod 301. The section 330 is thus tapered. It can also be seen that the stabilizing rod base body 303 is designed in the shape of a wave in the region 330, wherein the base body has elevations in the region of the cut-outs 331 and troughs in the region of the material elevation 332. The flexibility of the region 330 can thereby be influenced. It can also be seen that the base body of the stabilizing rod 301 tapers in the region 330 towards the material elevations 332, i.e. the base body is wedge-shaped. This design promotes easier bending of the rod, since the compression of the material is greatest in the region of the bending point. Thus, in this embodiment, this region is advantageously not only slotted, but also reduced in material thickness.

Figure 5:
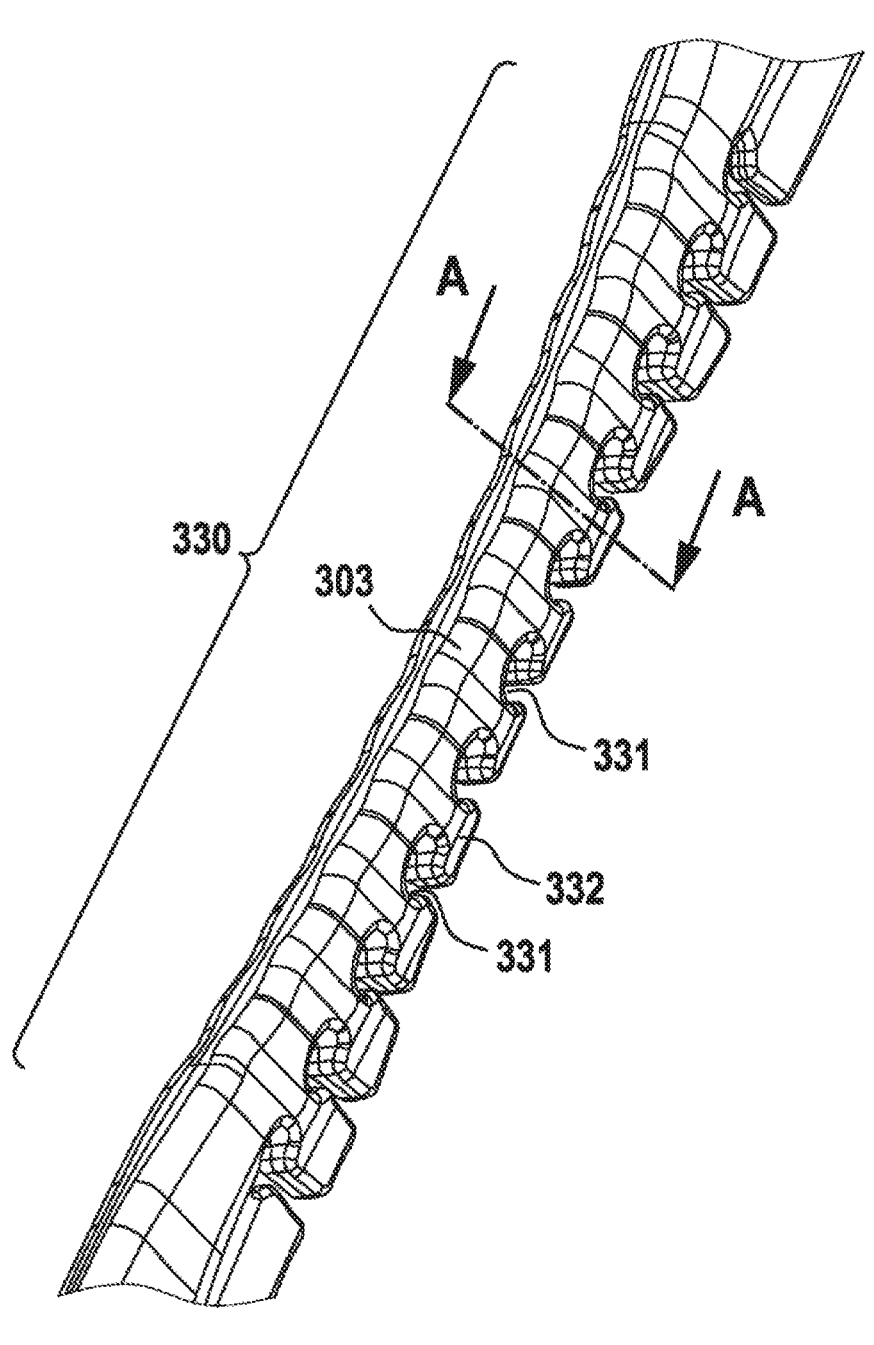
FIG. 5 shows the central section of the stabilizing rod from FIG. 3.

FIG. 5 shows a section of the stabilizing rod from FIG. 3 in the region of the third flexible section 330, which again has a base body 303 and material elevations 332 adjacent to it, through which cut-outs 331 are formed. The shapes of the section 330 and in particular of the base body 303, the material elevation 332 and the cut-out 331 described for FIGS. 3 and 4 can also be clearly seen here.

A cross-sectional line AA is also shown. The cross section AA can have not only the shape shown in FIGS. 3 to 5, but also various other shapes.

Such other shapes of the cross section A-A through the base body and one of the material elevations forming the cut-outs are shown by way of example in FIG. 6. FIG. 6a shows a rectangular base body 303a with rounded edges and a material elevation 332a which likewise has a simple rectangular basic shape. In FIG. 6b, the base body 303b again has a rectangular basic shape with rounded edges, wherein the tooth-like material elevation 332b is designed in the shape of an arrowhead. In FIG. 6c, the base body 303c is formed with a lesser material thickness and the tooth-like material elevation 332c is designed in the shape of a mushroom head. In FIG. 6d, the base body 303d has two grooves 341 and 342. These grooves or notches advantageously serve to minimize stress in the material used. They also help not only to bend the rod slightly in the bending direction of the knee joint, but also to bend the rod by 180 offset by 90 when pulling the bandage over the flat band-like side of the rod. This is because the patient usually removes a knee bandage, especially if there is no other grip (as shown in FIG. 3 as 313), in such a way that the patient grips the upper edge of a bandage and pulls it in the direction of the heel, just like taking off a knee sock. The material of the bandage is bent by 180° in order to then pull the bandage downwards in the bending direction. The improved flexibility of the rod thanks to the grooves 341 and 342 makes it easier to remove the bandage. The grooves enable a stabilizing rod to be bent not only in the bending direction through the cut-outs in the central region, but also in the 90° offset lateral direction. The tooth-like material elevation 332d is again designed in the shape of an arrowhead.

The invention claimed is:

1. A stabilizing rod (101) for an orthopedic aid (200), wherein the stabilizing rod (101) comprises, in a longitudinal direction, a first section (110) and a second section (120), the first section (110) and the second section (120) being connected to each other via a third, flexible section (130), characterized in that at least the third, flexible section (130) is tapered relative to the first section (110) and the second section (120), comprises a plurality of material cut-outs (131), wherein the tapering is in a width direction, a degree of tapering being nonconstant at locations corresponding to different material cut-outs (131), wherein the deeper the material cut-outs (131) are, the greater a distance of the material cut-outs (131) are from a central region of the third flexible section (130) and wherein the material cut-outs (131) consist of tooth-shaped material elevations lying between the material cut-outs, wherein the tooth-shaped material elevations are expanding on one side of the material cut-outs and smooth on an other side of the material cut-outs.

2. An orthopedic aid, comprising the stabilizing rod (101) according to claim 1.

3. The orthopedic aid according to claim 2, wherein the orthopedic aid is a knee joint bandage (200).

4. The orthopedic aid (200) according to claim 3, wherein the knee joint bandage (200) comprises the stabilizing rod (101) and an additional stabilizing rod (102), wherein the stabilizing rod (101) and the additional stabilizing rod (102) extends over a length of the knee joint bandage (200).

5. The orthopedic aid (200) according to claim 4, wherein the third flexible section (130) of the stabilizing rod (101) and the additional stabilizing rod (102) is at least at a level of the knee (307) when the knee joint bandage (200) is in an applied state.

6. The orthopedic aid according to claim 2, wherein the stabilizing rod (101) is in one piece and consists of a material, the material comprising a plastic, wherein the first section (110) and the second section (120) are less flexible than the third section (130), and wherein the orthopedic aid is a knee joint bandage (200).

7. The stabilizing rod (101) according to claim 1, wherein the orthopedic aid is a bandage.

8. The orthopedic aid (200) according to claim 7, wherein the bandage comprises a knee joint bandage (200).

9. The stabilizing rod (101) according to claim 1, wherein the stabilizing rod (101) is in one piece and consists of a material, the material comprising a plastic.

10. The stabilizing rod (101) according to claim 1, wherein the first section (110) and the second section (120) are less flexible than the third section (130).

11. The stabilizing rod according to claim 1, wherein the stabilizing rod (101) has a length, a width and a height, the width of the third flexible section (130) being less than the width of the first section and the second section.

12. The orthopedic aid (200) according to claim 1, wherein the plurality of material cut-outs are arranged on a single side of the stabilizing rod (101), the single side being an inner, concave side upon the stabilizing rod being bent.

13. The orthopedic aid (200) according to claim 1, wherein the tooth-shaped material elevations abut one another upon a bending force applied at least partially perpendicularly to the longitudinal direction.

14. The orthopedic aid (200) according to claim 1, wherein the material cut-outs correspond to a region of higher thickness.

15. The orthopedic aid (200) according to claim 1, wherein the third, flexible section (130) comprises grooves or notches configured to bend the stabilizing rod in a bending direction of a knee joint.

16. The stabilizing rod (101) according to claim 1, wherein the stabilizing rod is at least partially roughened.

17. The stabilizing rod (101) according to claim 1, wherein the third, flexible section (130) comprises thickened regions corresponding to locations of the material cut-outs and thinner regions corresponding to locations at which the material cut-outs are adjoined.

18. The stabilizing rod (101) according to claim 1, wherein a thickness of the stabilizing rod (101) is greater in the third, flexible section (130) compared to a thickness in the first section (110) and in the second section (120).

19. The stabilizing rod (101) according to claim 1, wherein the first section (110) comprises a gripping piece, and the gripping piece comprises an eyelet.

20. The stabilizing rod (101) according to claim 1, wherein the stabilizing rod is restricted from bending to a greater extent along a broad side of the stabilizing rod.

\* \* \* \* \*